Figure 1:
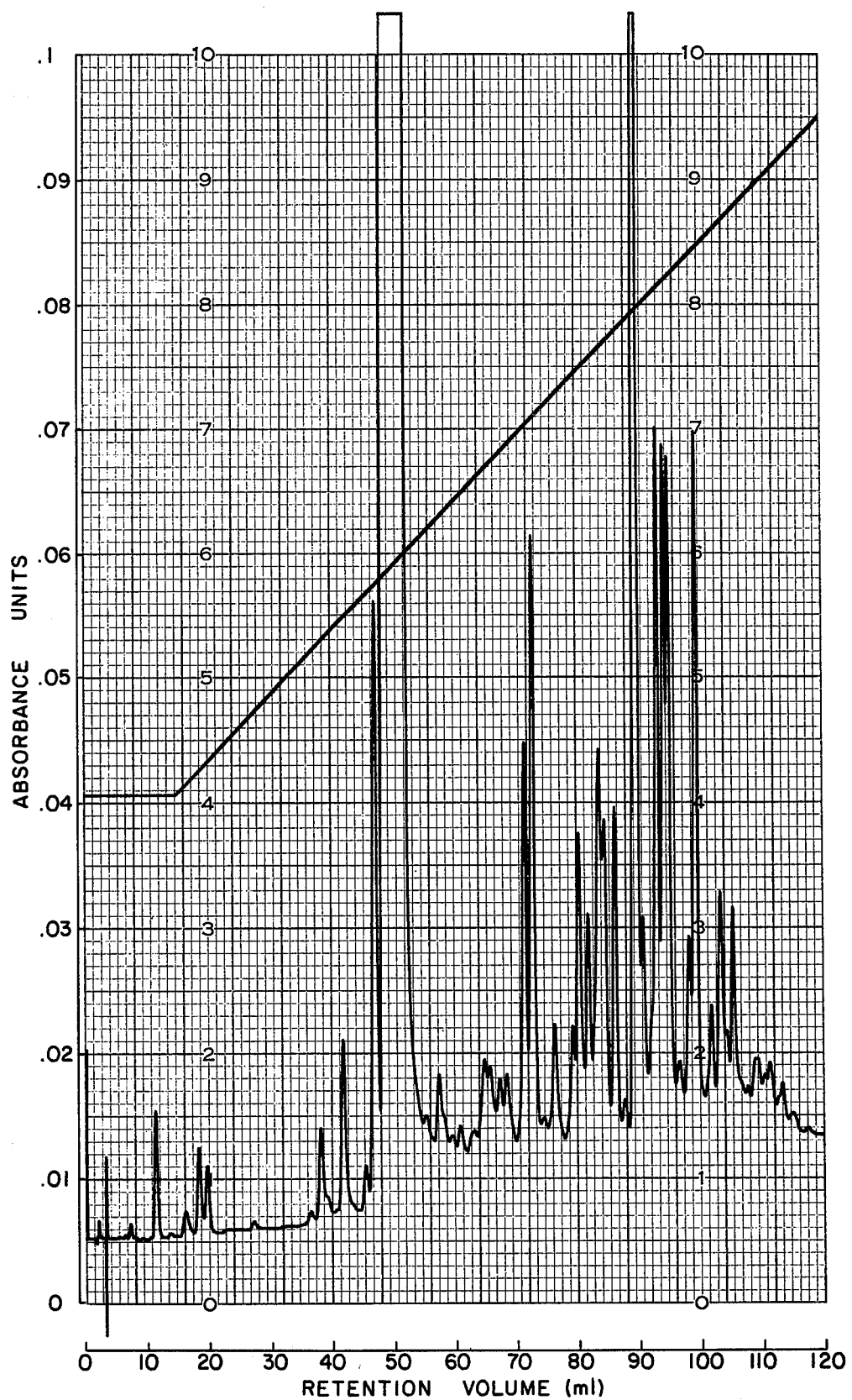

United States Patent [19]

Kinson

[11] 4,110,541

[45] Aug. 29, 1978

[54] METHOD FOR PURIFYING A DEHYDROCHLORINATION MIXTURE

[75] Inventor: Philip L. Kinson, Clifton Park, N.Y.

[73] Assignee: General Electric Company, Schenectady, N.Y.

[21] Appl. No.: 767,046

[22] Filed: Feb. 9, 1977

[51] Int. Cl.$^2$ ............................................. C07C 37/24
[52] U.S. Cl. ..................................................... 568/725
[58] Field of Search ..................................... 260/619 A

[56] References Cited

U.S. PATENT DOCUMENTS 3,856,556  12/1974  Brzozowski et al. ........... 260/619 A

*Primary Examiner*—Norman Morgenstern
*Attorney, Agent, or Firm*—William A. Teoli; Joseph T. Cohen; Charles T. Watts

[57] ABSTRACT

A method is provided for making substantially pure 1,1-dichloro-2,2-bis(4-hydroxyphenyl)ethylene by dehydrochlorinating 1,1,1-trichloro-2,2-bis(4-hydroxyphenyl)ethane with a methanol solution of potassium hydroxide, followed by purifying the crude reaction product with a mixture of a hot aromatic solvent and a polar solvent, such as methanol.

8 Claims, 2 Drawing Figures

METHOD FOR PURIFYING A DEHYDROCHLORINATION MIXTURE

The present invention relates to a method for purifying the dehydrochlorination product of 1,1,1-trichloro-2,2-bis(4-hydroxyphenyl)ethane resulting in the production of a substantially pure 1,1-dichloro-2,2-bis(4-hydroxyphenyl)ethylene. More particularly, the present invention relates to the use of a hot aromatic solvent, such as xylene, and a polar organic solvent, such as methanol, to effect the removal of dehydrochlorination contaminants.

As taught by Porejko and Wielgosz, Synthesis and Properties of Polycarbonates with Chloro Bisphenols, Polymeri, 13, (2), 55 (1968), Part I, Synthesis of Chloro Bisphenols and Their Chloroformic Derivatives, the potassium hydroxide-methanol dehydrochlorination procedure for dehydrochlorinating 1,1,1-trichloro-2,2-bis(4-hydroxyphenyl)ethane, referred to hereinafter as "trichloride," which has the formula,

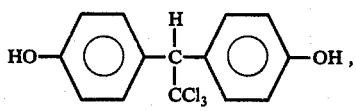

results in highly contaminated 1,1-dichloro-2,2-bis(4-hydroxyphenyl)ethylene, or "dichloride" of the formula,

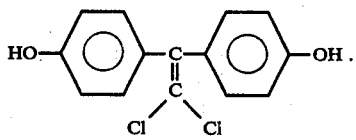

Dichloride contamination can arise when trichloride compounds, formed in making the trichloride are carried into the dehydrochlorination mixture. In addition, other compounds can be formed during dehydrochlorination. Included by the contaminating compounds in the dehydrochlorination mixture are the trichloride of formula (2) and one or more compounds of the formulas,

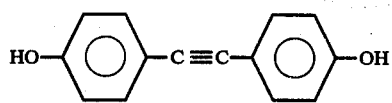

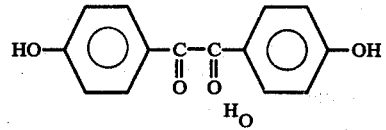

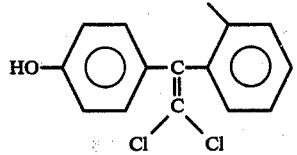

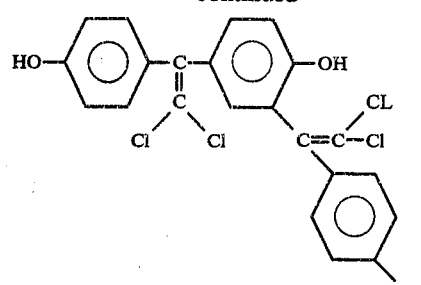

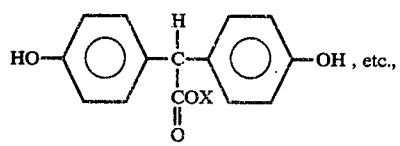

where X is hydrogen or methyl.

A convenient determination of dichloride purity is by use of liquid chromatography as discussed by Nina Hadden et al, Basic Liquid Chromatography (1971) by Varian Aerograph. The chromatogram shown by FIG. 1 was generated from the dehydrochlorination mixture of Porejko et al as defined above with a Waters Model 244 liquid chromatograph. A Waters Model 244 liquid chromatograph was used equipped with a Model U6K injector, a Bondapak $C_{18}$ column, a Model 440 detector equipped with a 10 mm cell and operated at 280 nm set at 0.1 AUFS (absorbance units full scale) and a 10 millivolt Houston Instrument Omniscribe recorder with a chart speed of 0.25 centimeters per minute. A 10 $\mu$l sample of a 10% (w/v) methanol solution of the dichloride was injected into the column and was eluted at 2 ml per minute, where the solvent mixture was programmed linearly over a 1 hour period from an initial composition of 40% methanol and 60% water to a final composition of 100% methanol.

In FIG. 1, the dichloride absorbance is shown at about 50–60 ml Retention Volume. A wide variety of other absorbances representing the above contaminants shown by formulas (1) and (3–7) and others are also shown.

In Polish Pat. No. 144,765, Wielgosz et al describe that improved dichloride purity can be achieved if lower mole ratios of KOH are employed for trichloride dehydrohalogenation, such as 6–8 moles of potassium hydroxide per mole of trichloride. A temperature of 40° C. to 50° C. is also recommended by Wielgosz et al. However, it has been found that a chromatogram generated by dichloride made in accordance with Polish Pat. No. 144,765 also contains a significant amount of absorbances other than the dichloride which exceed 60% of 0.1 AUFS.

In addition to using a chromatograph, another procedure which can be used to measure dichloride purity is by determining the absorbance value of dichloride with a Carey 14 Recording Spectrophotometer. The Porejko et al dichloride, which is found to be very dark in color, has an absorbance value of about 2 when measured as a methanol solution (2.50 grams/50 ml using a 10 cm cell in a Carey 14 Recording Spectrophotometer with light at 425 nm). The dichloride made in accordance with Polish Pat. No. 144,765 has been found to have an absorbance value of 1.24. The term "color-free" as used hereinafter in defining dichloride purity will indicate an absorbance value of less than 0.3 using a Carey 14 spectrophotometer as previously defined.

Figure 2:
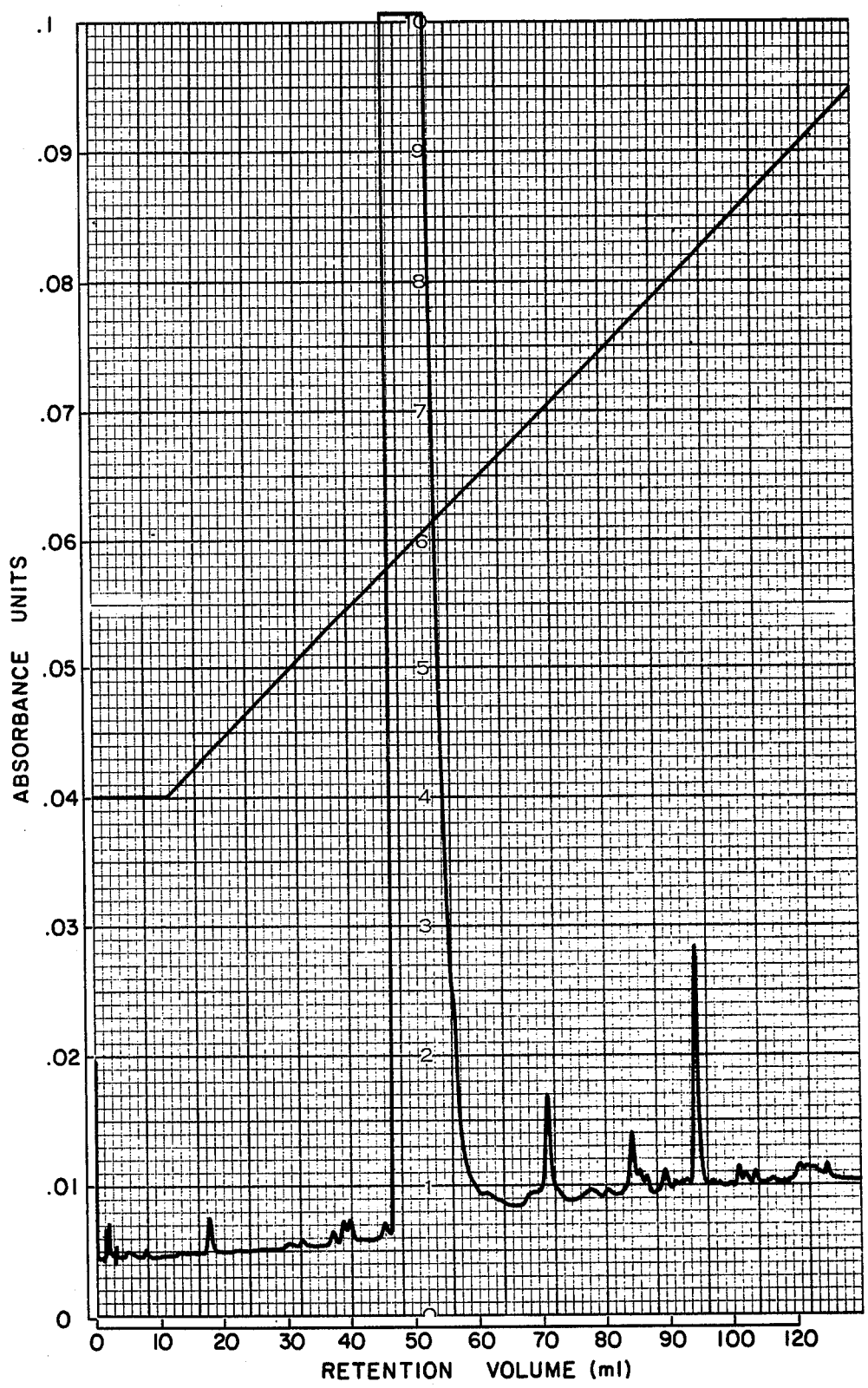

The present invention is based on the discovery that substantially pure dichloride capable of generating the chromatogram of FIG. 2, can be obtained by dissolving the dehydrochlorination reaction solids made by the procedure of either Porejko et al, or Polish Pat. No. 144,765 in a hot aromatic solvent, such as xylene, to produce a filterable solution, followed by the addition of small amounts of a polar organic solvent, such as methanol to the resulting filtrate while it is being cooled to effect the separation of substantially pure dichloride crystals. In addition, the dichloride is also found to be color-free as previously defined.

The present invention is based on the discovery that substantially color-free dichloride, which is capable of generating a liquid chromatogram as shown in FIG. 2, can be obtained by dissolving the dehydrochlorination reaction solids, made in accordance with Wielgosz et al or Polish Pat. No. 144,765, in a hot aromatic solvent, such as xylene, to product a filterable solution, followed by the addition to the resulting filtrate of a small amount of a polar organic solvent, such as methanol, to effect the separation of substantially pure color-free dichloride crystals.

There is provided by the present invention, a method for making a dichloride of formula (2) by the dehydrochlorination of the trichloride of formula (1) in a potassium hydroxide-methanol dehydrochlorination medium, whereby a contaminated dichloride is obtained, which method provides the improvement which comprises (1) dissolving the contaminated dehydrochlorination reaction product of the trichloride in an aromatic organic solvent at a temperature of at least 70° C.,
(2) filtering the solution of (1),
(3) adding to the filtrate of (2) up to 25% by weight of a polar solvent, based on the weight of the aromatic organic solvent,
(4) effecting the separation of dichloride crystals from the resulting mixture of (3) at a temperature in the range of from at least 10° below the temperature used to dissolve the dehydrochlorination reaction solids in step (1) to about 20° C.,
(5) collecting the resulting dichloride crystals formed in step (4) and
(6) drying the dichloride crystals at a temperature in the range of up to about 105° C.

Included by the aromatic organic solvents which can be used in the practice of the method of the present invention are xylene, toluene, benzene, chlorobenzene and mixtures thereof. Included by the polar organic solvents which can be used in the practice of the method of the present invention are, for example, methanol, ethanol, acetone, other $C_{(3-8)}$ aliphatic alcohols, diols, water, aliphatic organic nitriles, etc., and mixtures thereof.

In order that those skilled in the art will be better able to practice the method of the present invention, the following example is given by way of illustration and not by way of limitation. All parts are by weight.

EXAMPLE 1

A trichloride was made as follows in accordance with the teaching of Porejko et al:

A mixture of 885 grams of chloral and 108 grams of water was made and allowed to stand overnight to produce 993 grams of chloral hydrate.

There was added dropwise 1200 ml of a 1:1 (by volume) solution of glacial acetic acid and concentrated sulfuric acid to a solution maintained at 5°–10° C. of a mixture of the above chloral hydrate and 1250 grams of phenol in 1200 ml of glacial acetic acid. There was then added dropwise an additional 1500 ml of concentrated sulfuric acid. The additions were completed over a period of 3 hours. The reaction mixture was then stirred at 10° C. until crystals of product had precipitated. The mixture was then filtered and the resulting crude product was washed repeatedly with water. There was obtained an 89.5% yield of slightly pink crystals after the crude material was dried at 60° C. Based on method of preparation the product was the trichloride of formula (1).

The above trichloride was dissolved in 4.83 liters of absolute ethanol, heated to nearly reflux and 7.24 liters of water was added. The material was allowed to cool and crystallize overnight. The mixture was then filtered and the crude product dried at 60° C., resulting in 1329 grams of dichloride having a melting point of 202° C.

A solution of 254 grams of the above trichloride was dissolved in 4 liters of an aqueous solution of 3 normal potassium hydroxide. The resulting solution was warmed for 6 hours at 50° C. The resulting reaction mixture was then cooled and 4 liters of water were added. The mixture was then neutralized by slowly adding 10% aqueous hydrochloric acid. A white precipitate was formed which was filtered, washed with water and dried at 80° C. There was obtained a 90% yield of dichloride having a melting point of 215°–17° C. A chromatogram of the dichloride is shown by FIG. 1. The absorbance of the dichloride using 425 nm light in a Carey 14 spectrophotometer was found to be greater than 2.

Two hundred ten grams of the above dichloride crystals were dissolved in 3 liters of xylene at a temperature of 150° C. The resulting solution was filtered. There was added 50 ml of methanol to the filtrate while it was allowed to cool to room temperature. There was obtained a 94% yield of dichloride.

A chromatogram was made using a Waters Model 244 chromatograph in accordance with the above described procedure, which is shown by FIG. 2. In addition, the dichloride was found to be substantially colorless and was found to have an absorbance value of less than 0.3 using a Carey 14 spectrophotometer in accordance with the procedure previously defined.

Based on the results shown in my copending application RD-8859, one skilled in the art would expect that the dichloride made in accordance with the method of the present invention would provide a polycarbonate having substantially superior Notched Izod impact values as compared to the Notched Izod impact value obtained with a polycarbonate derived from the dichloride made in accordance with Wielgosz et al, measuring the Notched Izod impact values in accordance with ASTM procedure.

Although the above example shows only a few of the very many variables which can be used in practicing the method of the present invention, it should be understood that a much broader variety of aromatic organic solvents and polar organic solvents can be employed as shown in the description preceding this example.

Other procedures for effecting the removal of contaminants from trichloride dehydrochlorination reaction products are shown by Cleveland et al docket RD-7419, Philip L. Kinson docket RD-8859 and Kinson et al RD-8965, all assigned to the same assignee as the present invention.

What I claim as new and desire to secure by Letters Patent of the United States is:

1. In a method for making a dichloride of the formula,

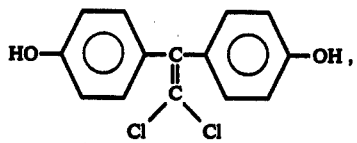

by the dehydrochlorination of a trichloride of the formula,

in a potassium hydroxide-methanol medium, whereby a contaminated dichloride dehydrochlorination reaction product is obtained, the improvement which comprises (1) dissolving the contaminated dehydrochlorination reaction product of the trichloride in an aromatic organic solvent selected from the class consisting of xylene, toluene, benzene, chlorobenzene and mixtures thereof at a temperature of at least 70° C., (2) filtering the solution of (1),
(3) adding to the filtrate of (2) up to 25% by weight of a polar solvent, selected from the class consisting of methanol, ethanol, acetone, $C_{(3-8)}$ aliphatic alcohols, diols, water, aliphatic organic nitriles and mixtures thereof, based on the weight of the aromatic organic solvent,
(4) effecting the separation of dichloride crystals from the resulting mixture of (3) at a temperature in the range of from at least 10° below the temperature used to dissolve the dehydrochlorination reaction solids in step (1) to about 20° C.,
(5) collecting the resulting dichloride crystals formed in step (4) and
(6) drying the dichloride crystals at a temperature in the range of up to about 105° C.

2. A method in accordance with claim 1, where the aromatic organic solvent is xylene.

3. A method in accordance with claim 1, where the polar organic solvent is methanol.

4. A method in accordance with claim 1, where the aromatic organic solvent is toluene.

5. A method in accordance with claim 1, where the aromatic organic solvent is benzene.

6. A method in accordance with claim 1, where the aromatic organic solvent is chlorobenzene.

7. A method in accordance with claim 1, where the polar organic solvent is acetone.

8. A method in accordance with claim 1, where the polar organic solvent is ethanol.

* * * * *